(12) United States Patent
Lim et al.

(10) Patent No.: US 8,431,627 B2
(45) Date of Patent: Apr. 30, 2013

(54) FILLER MATERIAL FOR CROWNS, CROWN MATERIAL CONTAINING SAME, AND METHOD OF MANUFACTURING THEREOF

(75) Inventors: Hyung Sup Lim, Ansan (KR); Hyung Joon Lim, Anyang (KR); Young Cheol Yoo, Ansan (KR); Sang Heon Kang, Ansan (KR); Jeong Won Seo, Koyang (KR)

(73) Assignee: Sukgyung AT Co., Ltd., Ansan (KR)

( * ) Notice: Subject to any disclaimer, the term of this patent is extended or adjusted under 35 U.S.C. 154(b) by 406 days.

(21) Appl. No.: 12/541,318

(22) Filed: Aug. 14, 2009

(65) Prior Publication Data

US 2010/0292364 A1 Nov. 18, 2010

(30) Foreign Application Priority Data

May 12, 2009 (KR) ........................ 10-2009-0041390

(51) Int. Cl.
*A61K 6/08* (2006.01)
*A61K 6/083* (2006.01)
*A61K 8/72* (2006.01)
*A61F 2/00* (2006.01)
*C04B 14/04* (2006.01)

(52) U.S. Cl.
USPC ........... 523/116; 106/489; 523/105; 523/113; 523/115

(58) Field of Classification Search ................... 523/116
See application file for complete search history.

(56) References Cited

U.S. PATENT DOCUMENTS

| 4,215,033 | A | * | 7/1980 | Bowen ........................ 523/115 |
| 6,620,861 | B1 | | 9/2003 | Nakatuka et al. |
| 6,623,856 | B1 | | 9/2003 | Kodas et al. |
| 6,709,271 | B2 | | 3/2004 | Yin et al. |
| 6,849,112 | B2 | | 2/2005 | Nishida et al. |
| 6,933,327 | B2 | | 8/2005 | Yamakawa et al. |
| 6,993,934 | B2 | | 2/2006 | Kodas et al. |
| 7,393,883 | B2 | | 7/2008 | Jones et al. |
| 2004/0134230 | A1 | * | 7/2004 | Kodas et al. .................... 65/17.2 |
| 2005/0147752 | A1 | * | 7/2005 | Kodas et al. ................. 427/249.1 |
| 2007/0142495 | A1 | | 6/2007 | Neffgen et al. |
| 2007/0208123 | A1 | * | 9/2007 | Kambe et al. .................. 524/432 |
| 2008/0044488 | A1 | * | 2/2008 | Zimmer et al. ................. 424/600 |
| 2008/0119585 | A1 | | 5/2008 | Van Lelieveld et al. |

FOREIGN PATENT DOCUMENTS

EP 475239 A2 * 3/1992

OTHER PUBLICATIONS

Rheinberger et al., Computer generated English translation of EP 475239 A2, Mar. 18, 1992.*

* cited by examiner

*Primary Examiner* — Peter F Godenschwager
*Assistant Examiner* — David Karst
(74) *Attorney, Agent, or Firm* — Bishop & Diehl, Ltd.

(57) ABSTRACT

The present invention provides a composition for crown material including resin and a fine spherized composite glass powder. The fine composite glass powder of the present invention for such a configuration has superior qualities with regard to both sintering and optical characteristics, and can be used as a filler for crown material.

10 Claims, 1 Drawing Sheet

FILLER MATERIAL FOR CROWNS, CROWN MATERIAL CONTAINING SAME, AND METHOD OF MANUFACTURING THEREOF

CROSS-REFERENCE TO RELATED APPLICATIONS

This application claims priority to Korean application number 10-2009-0041390, filed on May 12, 2009, which is incorporated herein by reference.

TECHNICAL FIELD

The present invention relates to a composition for crown material, and more specifically to a filler material for crown use having superior sintering and optical characteristics, and to a crown material composition containing same and a manufacturing method thereof.

BACKGROUND OF THE INVENTION

In the field of crown materials there is a rapid increase in the use of fine powders, particularly ceramic powders. In particular, the use of fine composite glass powders used as dental filler is increasing rapidly with the aging of society. In addition, the improvement of quality is becoming recognized as an important task as the use of these fine ceramic powders increases. Here "quality" refers the sintering characteristics, optical characteristics, and mechanical characteristics of the fine powder, and is determined by the size, shape and composition of the basic material. Accordingly, in order to improve the quality of fine powders, it is key to establish technologies for controlling the size, shape and composition of the fine powder. These fine glass powders are composed of comparatively low-cost ingredients, and high-value-added products can be made by increasing quality; the high-priced powder products currently on the market are seeing raising demand despite their non-spherical shape.

Currently, the manufacture of glass powders used as dental filler takes place by producing a fine powder form through a process of crushing after first melting the crown component glass with a suitable composition. The fine powders thus produced have a size typically of several μm, and because they have a sharp, non-spherical shape, their sintering and optical characteristics are problematically poor.

SUMMARY OF THE INVENTION

Task of the Invention

The present invention has been devised in order to resolve the problems of the prior art as described hereinabove; the objective thereof is to provide a filler material for use in dental crowns having improved sintering and optical characteristics through the spherization of the shape (i.e., spherical) of a fine composite-glass powder.

Another objective of the present invention is to provide a composition for crown material having improved sintering and optical characteristics.

A further objective of the present invention is to provide a method of manufacturing a composition for crown material having improved sintering and optical characteristics.

Means of Resolving Problem

The above-described technical task of the present invention is accomplished by the following means: (1) A filling material for crowns including nano-sized spherical composite glass powder; (2) A crown material composition including resin and the filler material of Paragraph 1; (3) The crown material composition of Paragraph 2, wherein the discrepancy in the refractive index of the particles forming the spherical composite glass powder and the refractive index of the resin is 0.1 or less; (4) The crown material composition of Paragraph 2, wherein the refractive index of the particles comprising the spherical composite glass powder is 1.45-1.65; (5) The crown material composition of Paragraph 2, wherein the refractive index of the particles comprising the spherical composite glass powder is 1.52-1.56; (6) The crown material of Paragraph 2, wherein the average diameter of the spherical composite glass powder is 0.2-20 μm; (7) The crown material of Paragraph 2, wherein the average diameter of the spherical composite glass powder is 0.4-2.0 μm; (8) The crown material of Paragraph 2, wherein the composition of the spherical composite glass powder includes BaO, $Al_2O_3$, $SiO_2$, and $B_2O_3$; (9) The crown material of Paragraph 2, wherein the spherical composite glass powder composition comprises: BaO 28±10 wt %; $Al_2O_3$ 9±3 wt %; $SiO_2$ 47±10 wt %; and $B_2O_3$ 15±3 wt %; (10) The crown material of Paragraph 2, wherein the composition of the spherical composite glass powder includes SrO, $Al_2O_3$, $SiO_2$, and $B_2O_3$; (11) The crown material of Paragraph 2, wherein the spherical composite glass powder composition comprises: SrO 25±10 wt %; $Al_2O_3$ 13±5 wt %; $SiO_2$ 48±8 wt %; and $B_2O_3$ 14±3 wt %; (12) The crown material composition of either of Paragraph 9 or Paragraph 11, wherein F, ZnO, and $TiO_2$ are present at no more than 1 wt %; (13) The crown material composition of Paragraph 2, wherein the spherical composite glass powder is spherized by applying flame-spraying technique to a composite glass powder; (14) A method of manufacturing a crown material composition by blending of a spherical composite glass powder with resin.

EFFECT

According to the present invention, a crown material composition is provided having improved optical and sintering characteristics through the addition of a nano-sized spherical composite glass powder as a crown filling material.

Other embodiments, systems, methods, features, and advantages of the present invention will be, or will become, apparent to one having ordinary skill in the art upon examination of the following drawings and detailed description. It is intended that all such additional systems, methods, features, and advantages be within the scope of the present invention, and can be protected by the accompanying claims.

DETAILED DESCRIPTION

Figure 1:
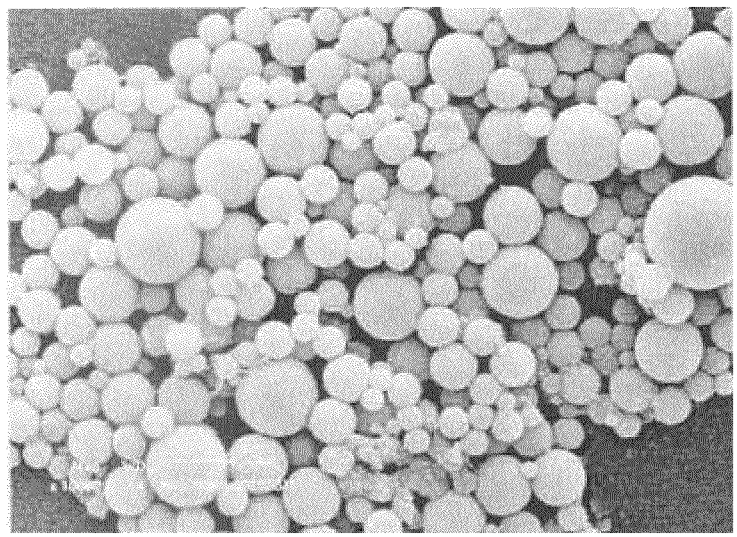
FIG. 1 is an electron microscope photograph of the nano-sized spherical composite glass powder manufactured according to Embodiment 1 of the present invention.

The following descriptions of detailed embodiments are for exemplifying the principles and advantages of the inventions claimed herein. They are not to be taken in any way as limitations on the scope of the inventions.

The fine nano-sized composite glass powder of the present invention comprises spherical particles, unlike the non-spherical fine particles that had been used in the crown filling materials of the prior art, and has superior sintering and optical characteristics.

The particle diameter of the fine, nano-sized spherical composite glass powder is an average of 0.2-20 μm, and preferably 0.4-20 μm. If the diameter is less than 0.2 μm, the specific surface area will be too great and there will be a risk of blending with the resin; if it exceeds 20 μm, the weight will be so great that there is a risk of precipitation when blending with resin. It is most preferable that the particle radius of the fine powder be 0.4-2.0 μm.

The refractive index, which determines the optical characteristics of said fine, nano-sized spherical composite glass powder, may be determined depending on the resin with which it is to be used; the difference between the refractive indices of the resin and the composite glass powder should be within 0.1, and preferably no more than 0.05. In the event of departure from the above range, the great difference from the refractive index of the resin will pose a risk of lost transparency and turbidity.

It is preferable that the refractive index of the fine, nano-sized spherical composite glass powder be 1.45-1.65, and even more preferable that it be 1.52-1.56. The restriction of the refractive index to this range is for the reason that the majority of resins currently on the market have refractive indices within this range.

The above-described refractive index of the fine, nano-sized spherical composite glass powder may be changed depending on the composition thereof, and the composition ratios.

By way of an example of the glass composition that can be used in the present invention, the specific compositions disclosed in Japanese Laid-Open Patents 2008-023003, 206-069924, 2002-275017, 2000-143430, 2000-102548, Heisei 8-225423, Heisei 7-033476, Heisei 3-047107, and Showa 56-152408 may be cited in their entirety.

In terms of preferability, as a first example composition of the composite powder of the present invention is provided a glass composition comprising BaO, Al2O3, SiO2, and B2O3; as a second example composition is provided a glass composition comprising SrO, Al2O3, SiO2, and B2O3.

The aforementioned first example composition of the present invention should preferably comprise: (a) BaO 28±10 wt %; (b) Al2O3 9±3 wt %; (c) SiO2 47±10 wt %; and (d) B2O3 15±3 wt %.

In addition to the above-listed primary components, ZnO, TiO2, and F may be added as additives at no more than 1 wt %.

It is preferable that the fine composite powder composition of the second example composition of the present invention comprise: (a) SrO 25±10 wt %; (b) Al2O3 13±5 wt %; (c) SiO2 48±8 wt %; and (d) B2O3 14±3 wt %.

In addition to the above-listed primary components, ZnO, TiO2, and F may be added as additives at no more than 1 wt %.

In the above embodiments, the respective quantity of BaO or SrO mixed in is added in order to obtain optimal X-ray absorption.

Al2O3 is added as a vitrifier and stabilizer; the reason for the quantity thereof being limited as in the example compositions is that if the upper limits in each composition are exceeded, the melting point rises excessively and there is a risk of increasing the processing temperature; while if added at less than the lower limit, there is a risk of an adverse impact on stability and curing, which is not preferable.

If the proportion of SiO2 exceeds the upper limit in the respective example compositions above, the melting point will increase, which will result in an increased admixture of impurities from the lining of the container into the glass; if it is added at less than the lower limit, there is a risk that the transparency will suffer, which is not preferable.

B2O3 is added as a flux; and acts to lower the melting point. In each of the above example compositions, the reason for its range being limited is that if the upper limit is exceeded in each composition, there is a risk of worsening the hydrolytic stability with respect to glass; if added at less than the lower limit, there is a risk that the melting point will increase, which will result in an increased admixture of impurities from the lining of the container into the glass; which is not preferable.

The fine, nano-sized spherical composite glass powders of the present invention, included within the above-described composition range, have superior enhancement in X-ray imaging, as well as superior sintering characteristics and transparency, so that they exhibit characteristics that are highly suitable for a filler used in crown material.

In addition, the present invention includes a composition for use in dental crowns that includes a fine, nano-sized spherical composite-glass powder.

The composition for use in dental crowns of the present invention comprises a resin and an inorganic filler such as described above. Here the proportion of the aforementioned filler of the present invention should preferably be in the 1-50 wt % range. If the proportion of the filler of the present invention is less than 1 wt %, not only will the significance of adding the inorganic filler be minimal, but this may also give rise to increased manufacturing costs, while if 50 wt % is exceeded, improved effects from the increased admixture are unlikely; thus it is best to remain within the above range. However, the above range does not have the significance of a boundary, but is rather a presentation of preferable conditions for implementation; thus, it must be borne in mind that the present invention can still be implemented even beyond this range.

There is no particular restriction on the type of resin used in the crown composition of the present invention. Accordingly, any type of resin that is in general use as a crown material of the prior art may be used. In the case of most resins that are on the market and in use currently, ordinarily the refractive index is in the range of 1.5-1.6. Specific examples of such resins include the ultraviolet-cured resins having epoxy resin, polyvinyl ester, polymethacrylate or acrylate, methacrylate, 2,2-bis[4(3-methacryloxy-2-hydroxypropoxy)phenyl]propane (bis-GMA), urethane methacrylate, alkanediol methacrylate, or cyanoacrylate as a base.

The fine, nano-sized spherical composite-glass powder used in the present invention can be manufactured by flame-spraying. The flame-spraying method involves adding a mixture comprising the raw powder, gas fuel, oxidizing gas, and shutoff gas to a flame burner and melting the fine, nano-sized composite-glass powder in the flame, and then spherizing this by surface tension as it is cooled.

In the present invention, it is acceptable to use a method of supplying the raw powder and fuel gas separately to the flame, and also to use a free-mix method that supplies the pre-mixed raw powder and fuel gas to the flame. An example of a flame-spraying burner device that can be employed in the latter case is disclosed in Korean Patent Gazette No. 10-0404350; in the present invention, it is sought to cite the device disclosed in that document.

The flow of the respective gases and the size of the spraying tube to be used in the above device may be determined according to the mass and size of fine powder added power hour. In other words, the length of the flame must be changed depending n the time for which the fine powder remains in the flame; the melting of the fine powder depends on the temperature distribution and the speed of the fine powder within the flame.

More specifically, one example of a method that can be employed in the manufacture of the fine, nano-sized spherical composite-glass powder of the present invention is disclosed in Korean Patent Gazette No. 10-0407506. The various operating conditions with regard to the quantity of fuel gas added to the furnace, the quantity of fuel gas added to the furnace, the quantity of carrier added to the furnace, the meting conditions and speed of spraying of the fuel, the ratio of raw material to fuel gas (P/V), the range of fuel speed and spraying speed, and the temperature conditions of the furnace walls, disclosed in the embodiments of that document, may be cited in their entirety in the present invention.

The above-described operating conditions being suitable to a manufacturing design for large quantities of fine powder, an example of the process conditions which might be implemented in a pilot unit could be downscaled to LPG 2-5 mL/min (5 mL/min in an air flowmeter) fuel gas, 2-4 mL/min (25 mL/min in an air flowmeter) and 5-15 mL/min compressed carrier gas (25 mL/min in an air flowmeter); with the flame formed to spray by scattering the raw powder at 1-3 g/hr with compressed air so as to perform spherical melting.

The other apparatus for manufacture of the fine, nano-sized spherical composite-glass powder of the present invention may be any commonly-known apparatus such as a fine-powder aerosol supply apparatus or an apparatus for capture of fine, nano-sized spherical particles may be used, either as-is or partially adjusted; thus, the detailed description thereof is omitted here.

Hereinbelow, preferred embodiments are presented in order to assist the understanding of the present invention; however, the embodiments hereinbelow merely exemplify the present invention, and the scope of the present invention is not limited to the below embodiments.

Embodiment 1

Manufacture of Fine, Nano-Sized Spherical Composite-Glass Powder

Using an altered burner of the type presented in Korean Patent No. 10-0404350, LPG 3 mL/min (5 mL/min in an air flowmeter) fuel gas, 3 mL/min (25 mL/min in an air flowmeter) and 10 mL/min compressed carrier gas (25 mL/min in an air flowmeter) was used; with the flame formed to spray by scattering the raw powder at 2 g/hr with compressed air so as to perform spherical melting.

The raw powder used in the present embodiment was $BaCO_3$, converted to 28 wt % BaO, together with 9 wt % $Al_2O_3$, 47 wt % $SiO_2$, 15 wt % $H_3BO_3$ converted to $B_2O_3$, and 1 wt % KF converted to F; this was completely melted at 1350° C. and cooled to obtain glass, which was crushed and classified to produce uniform spherical particles.

Embodiment 2

Manufacture of Fine, Nano-Sized Spherical Composite-Glass Powder

A fine, nano-sized spherical composite-glass powder was produced under the same conditions and processes as in Embodiment 1, except that the proportions used were 18 wt % $BaCO_3$ converted to BaO, 12 wt % $Al_2O_3$, 51 wt % $SiO_2$, 18 wt % $H_3BO_3$ converted to $B_2O_3$, and 1 wt % ZnO.

Embodiment 3

Manufacture of Fine, Nano-Sized Spherical Composite-Glass Powder

A fine, nano-sized spherical composite-glass powder was produced under the same conditions and processes as in Embodiment 1, except that the proportions used were 38 wt % $BaCO_3$ converted to BaO, 9 wt % $Al_2O_3$, 37 wt % $SiO_2$, 15 wt % $H_3BO_3$ converted to $B_2O_3$, and 1 wt % $TiO_2$.

Embodiment 4

Manufacture of Fine, Nano-Sized Spherical Composite-Glass Powder

A fine, nano-sized spherical composite-glass powder was produced under the same conditions and processes as in Embodiment 1, except that the proportions used were 25 wt % $SrCO_3$ converted to SrO, 13 wt % $Al_2O_3$, 48 wt % $SiO_2$, 13 wt % $H_3BO_3$ converted to $B_2O_3$, and 1 wt % F.

Embodiment 5

Manufacture of Fine, Nano-Sized Spherical Composite-Glass Powder

A fine, nano-sized spherical composite-glass powder was produced under the same conditions and processes as in Embodiment 1, except that the proportions used were 15 wt % $SrCO_3$ converted to SrO, 13 wt % $Al_2O_3$, 56 wt % $SiO_2$, 15 wt % $H_3BO_3$ converted to $B_2O_3$, and 1 wt % ZnO.

Embodiment 6

Manufacture of Fine, Nano-Sized Spherical Composite-Glass Powder

A fine, nano-sized spherical composite-glass powder was produced under the same conditions and processes as in Embodiment 1, except that the proportions used were 35 wt % $SrCO_3$ converted to SrO, 8 wt % $Al_2O_3$, 45 wt % $SiO_2$, 11 wt % $H_3BO_3$ converted to $B_2O_3$, and 1 wt % $TiO_2$.

Experiment 1

Figure 2:
FIG. 2 is an electron microscope photograph of the nano-sized spherical composite glass powder manufactured according to Embodiment 4 of the present invention.

Electron microscopy images of particles manufactured according to the above Embodiments 1 and 4 of the present invention are shown in FIGS. 1 and 2. As can be confirmed from said photographs, the shape of the microparticles of composite glass manufactured according to the present invention is perfectly spherical.

Experiment 2

The refractive index of the composite-glass microparticles manufactured according to each of the above embodiments was measured at a wavelength of 587 nm, and with regard to X-ray opacity, the aluminum equivalent thickness (AG) was measured according to DIN ISO 4049 and the results are shown in Table 1 below.

TABLE 1

|  | Embodiment 1 | Embodiment 2 | Embodiment 3 | Embodiment 4 | Embodiment 5 | Embodiment 6 |
| --- | --- | --- | --- | --- | --- | --- |
| BaO (wt %) | 28 | 18 | 38 | — | — | — |
| SrO (wt %) | — | — | — | 25 | 15 | 35 |
| Al2O3 (wt %) | 9 | 12 | 9 | 13 | 13 | 8 |
| SiO2 (wt %) | 47 | 51 | 37 | 48 | 56 | 45 |
| B2O3 (wt %) | 15 | 18 | 15 | 13 | 15 | 11 |
| F (wt %) | 1 | — | — | 1 | — | — |
| ZnO (wt %) | — | 1 | — | — | 1 | — |
| TiO2 (wt %) | — | — | 1 | — | — | 1 |
| Total | 100 | 100 | 100 | 100 | 100 | 100 |
| Refractive index (n) | 1.53 | 1.52 | 1.53 | 1.54 | 1.53 | 1.54 |
| AG (mm) | 3.2 | 3.3 | 3.1 | 3.3 | 3.2 | 3.2 |

As can be seen from the above experimental results, the filler material for dental crowns of the present invention has superior refractive indices and transparency when mixed with resin, and can therefore provide the same esthetic appearance as real teeth.

Hereinabove an explanation was provided with reference to the preferred embodiments of the present invention, but a person of skill in the art will understand that it is possible to alter and change the present invention in diverse ways without departing from the idea and scope of the present invention as set forth in the claims below.

What is claimed is:

1. A dental composition comprising:
   a resin; and
   an inorganic filler material comprising a composite glass powder;
   wherein the composite glass powder has a generally spherical shape, is usable in a human mouth and comprises approximately 18 wt % BaO; approximately 9 wt % Al2O3; approximately 47 wt % SiO2; approximately 15 wt % B2O3 and approximately 1 wt % F—.

2. The dental composition of claim 1, wherein the composite glass powder has a refractive index between approximately 1.45-1.65.

3. The dental composition of claim 1, wherein the composite glass powder has a refractive index between approximately 1.52-1.56.

4. The dental composition of claim 1, wherein an average particle diameter of the composite glass powder is between approximately 0.2-20 μm.

5. The dental composition of claim 4, wherein the average particle diameter is between approximately 0.4-20 μm.

6. The dental composition of claim 1, wherein a refractive index of the composite glass powder and a refractive index of the resin differ by no more than approximately 0.1.

7. The dental composition of claim 6, wherein the refractive index of the composite glass powder and the refractive index of the resin differ by no more than approximately 0.05.

8. The dental composition of claim 1, wherein the inorganic filler material comprises between approximately 1-50 wt % of the dental composition.

9. A dental composition comprising:
   a resin; and
   an inorganic filler material comprising a composite glass powder;
   wherein the composite glass powder has a generally spherical shape, is usable in a human mouth and comprises approximately 18 wt % BaO; approximately 12 wt % Al2O3; approximately 51 wt % SiO2; approximately 18 wt % B2O3 and approximately 1 wt % ZnO.

10. A dental composition comprising:
    a resin; and
    an inorganic filler material comprising a composite glass powder;
    wherein the composite glass powder has a generally spherical shape, is usable in a human mouth and comprises approximately 38 wt % BaO; approximately 9 wt % Al2O3; approximately 37 wt % SiO2; approximately 15 wt % B2O3 and approximately 1 wt % TiO2.

* * * * *